(12) United States Patent
Kerschmann et al.

(10) Patent No.: US 6,409,774 B1
(45) Date of Patent: Jun. 25, 2002

(54) ELECTROPHORESIS-ASSISTED STAINING OF MATERIALS

(75) Inventors: Russell L. Kerschmann, Mill Valley; Ronald Odom, San Francisco; Thomas Kuwahara, San Francisco; Mark Reddington, San Francisco, all of CA (US)

(73) Assignee: Resolution Sciences Corporation, Corte Madera, CA (US)

(*) Notice: Subject to any disclaimer, the term of this patent is extended or adjusted under 35 U.S.C. 154(b) by 0 days.

(21) Appl. No.: 09/330,400

(22) Filed: Jun. 11, 1999

(51) Int. Cl.[7] ............... G01N 27/26; G01N 27/447; D06P 5/20
(52) U.S. Cl. .............. 8/444; 204/450; 204/600
(58) Field of Search ............... 8/444; 204/450, 204/600

(56) References Cited

U.S. PATENT DOCUMENTS 4,707,236 A 11/1987 Borowsky ............. 204/456

OTHER PUBLICATIONS

M.V. Korytov & E. A. Kalacheva, "A device for electrophoretic staining and decolorization of slab polyacrylamide gels" Lab. Delo vol. 4 pp. 231–2, 1986.*

Andrews, "Electrophoresis: Theory, Techniques and Biochemical and Clinical Applications" Second Edition, Oxford University Press, New York, NY (1981).

Murphy, "Innovations: Fetal Sexing—A Report on the Process and Its Impact to Clients" *World Equine Veterinary Review*, vol. 2: full text (1997).

BIORAD Laboratories, "Model 175 Tube Cell Instruction Manual" Catalog No.165–1980. pp. i–12.

Pethig, "Dielectric Properties of Body Tissues" *Clin. Phys. Physiol. Meas.*8:5–12 (1987).

Querido, "Postmortem Changes in Electrical Resistance of the Gastric Wall During the Early Postmortem Period in Rats" *Forensic Science International*53:81–92 (1992).

* cited by examiner

*Primary Examiner*—Jill Warden
*Assistant Examiner*—John S. Starsiak, Jr.
(74) *Attorney, Agent, or Firm*—Clark & Elbing LLP

(57) ABSTRACT

A method for en bloc staining a biological sample by (a) immersing the sample in a staining solution including an ionically conductive solution and a charged stain molecule or stain precursor that associates with a component of the sample; and (b) applying an electric field across the staining solution, whereby the stain molecule penetrates into the sample. Staining times are reduced.

20 Claims, 2 Drawing Sheets

ELECTROPHORESIS-ASSISTED STAINING OF MATERIALS

BACKGROUND OF THE INVENTION

This invention relates to the staining of biological samples for imaging.

The preparation of organic tissue samples and other materials for transmission microscopy, both visible light and electron microscopy, is normally carried out by subjecting the sample to a series of chemical treatments culminating in the production of a solid block in which the sample is embedded.

In a conventional tissue preparation process, the tissue is first chemically fixed with formalin, glutaraldehyde, or other material which serves to preserve the sample from autolysis (self-degradation), to render the sample rigid, and to increase its permeability, thereby enhancing the infiltration of the subsequent solutions. The infiltration steps which follow chemical fixing remove all of the water from the sample through progressive replacement of water with increasing concentrations of solvents such as alcohol and xylene. Infiltration is followed by treatment with melted paraffin and the sample then is cooled to room temperature whereupon it solidifies. Alternatively, the tissue is infiltrated with plastic polymer that is then hardened by heat, ultraviolet light or other means. The hardened, infiltrated tissue is then position in a mold and surrounded with paraffin or plastic to produce a tissue block.

The block containing the tissue is sectioned on a microtome. In the case of light microscopy, the sections are collected and placed on glass slides. Once secured on the slides, the sections are then stained with any number of dyes which label particular parts of the cell (e.g., nucleic acids, lipids, etc.) or, alternatively, are processed for immunohistochemistry.

Alternatively, methods are available for en bloc staining, wherein the entire sample is stained by immersion, prior to being subjected to infiltration and embedment to produce the tissue block. Sections are then cut from the block for transmission microscopy, or the cut face of the block itself is imaged in a process called block face microscopy. In the latter case, including that implemented in the Surface Imaging Microscope (U.S. Pat. No. 4,960,330, "Image Recording Apparatus"), a sample that has been stained en bloc is subsequently infiltrated by and embedded in a medium that is heavily opacified or otherwise treated to allow for the suppression of images of tissue originating from more than a few microns deep in the block. This results in the production of a thin, "virtual section" closely resembling a conventional glass-slide mounted tissue section.

Because the volume of material imaged in a block face microscopy is large relative to the much thinner section of material used in conventional glass slide-based technology, en bloc staining must accomplish penetration through a greater thickness of material. This circumstance results in an undesirable increase in sample preparation time.

Methods employed to accelerate the penetration of stain into the tissue in en bloc staining include the proper choice of fixative; the application of heat, microwave radiation, vacuum or ultrasound; and the addition of detergents and other chemicals to the staining solutions. However, even with the use of such methods, the penetration of stains into relatively large volumes of tissue can require times measured in days or even weeks. Penetration times become even greater when the stain molecule or stain precursor is conjugated with large carrier molecules, such as are used in the practice of immunohistochemistry.

SUMMARY OF THE INVENTION

In general, the invention features a means for increasing the rate and extent of penetration of a component used in staining into a biological tissue by use of electrophoresis. Electrophoresis refers to a process in which charged molecules are caused to migrate in a fluid under the influence of an electric field. The stain or components used in staining include free dyes or colorant reagent molecules, chemical conjugates with antibodies, nucleic acid probes and other high molecular weight carrier molecules, e.g. antibodies.

The invention features a method for en bloc staining a biological sample, including the steps of (a) immersing the sample in a staining solution including an ionically conductive solution and a charged stain molecule or stain precursor that associates with a component of the sample; and (b) applying an electric field across the staining solution, whereby the stain molecule or precursor migrates through the sample. Penetration of the stain into the sample is enhanced.

Another feature of the method of the invention includes (c) immersing the primary antibody-containing sample in a staining solution including an ionically conductive solution and a charged secondary antibody that binds to the primary antibody; and (d) applying an electric field across the staining solution. Penetration of the secondary antibody into the tissue is enhanced.

In another embodiment of the invention, the primary antibody-containing sample is immersed in a solution comprising a secondary antibody that binds to the primary antibody.

In one embodiment of the invention, the sample is infiltrated with a gel support prior to immersing the sample in the staining solution.

In preferred embodiments, a voltage in the range of 50–700V, and preferably 100–400 V, is applied. The electric field is maintained for a time in the range of 1 to 25 hours, and preferably, 3 to 15 hours.

In other preferred embodiments, the staining solution comprises both a stain precursor and a stain molecule, or primary and secondary antibodies, where the pair of molecules is selected to migrate in opposite directions in an electric field. One of the components, for example, a stain precursor, is introduced into the staining solution on a first side of the sample and the second component, for example, a stain molecule, is introduced into the staining solution on the opposing side of the sample.

In another aspect of the invention, the proportion of unbound stain molecule in a sectioned tissue is reduced by (a) first immersing the tissue sample to in a staining solution including an tonically conductive solution and a stain precursor that associates with a component of the sample; and (b) then applying an electric field across the staining solution, whereby penetration of the stain precursor into the sample and emigration of unbound stain precursor from the sample occurs.

The term "sample" is used herein to refer to the tissue or other material which is to be stained and embedded. The sample, prior to staining, has not been prepared by microtomy. The thickness of a sample typically is greater than 200 microns, and can be greater than one millimeter, one centimeter, or more.

The terms "stain" or "stain molecule" are used herein to refer to a dye, reagent, or other material for producing coloration in tissues or microorganisms for microscopic examination. The stain may be a free dye or colorant reagent molecule or it may be a dye or reagent bound to antibodies, nucleic acid probes, lectins or other large carrier molecules that have a specific affinity for a component of the sample. Colorant reagent molecules include dye precursors which react to provide observable color or fluorescence.

The term "stain precursor" is used herein to refer to a carrier molecule having specific affinity for a compound which is unlabeled, i.e., does not include a dye or colorant reagent. In order to visualize the tissue, the stain precursor is complexed with a second labeled compound to form a multi-molecular conjugate. Such a stain conjugate may include a primary compound, e.g., a primary antibody having an affinity for a component of the tissue, which itself is not observed by conventional imaging techniques, and a secondary compound, e.g., a secondary antibody having affinity for the primary antibody, e.g., an anti-immunoglobulin antibody, which bears a dye or colorant reagent used to image the tissue or an enzyme which converts a colorless substrate into a colored substrate.

The term "component of the sample or tissue" is used herein to refer to the epitope or other region within the tissue that preferentially interacts with the stain or some portion thereof.

BRIEF DESCRIPTION OF THE DRAWINGS

The invention is described with reference to the figures, which are presented for the purpose of illustration only and in which.

DESCRIPTION OF THE PREFERRED EMBODIMENT

Tissue staining using antibodies appropriately labeled for subsequent detection is a versatile imaging technique due to the specificity of the antigen-antibody binding process. Antibody staining can reveal both the presence and subcellular location of the antigen of interest, thereby permitting imaging of the subcellular components of the tissue.

Antibody staining poses significant problems when applied to samples of significant volume because binding is diffusion-dependent. The antibody must first diffuse into the tissue before binding, which can take days and even weeks in larger tissue samples. Long staining times may have a deleterious effect on tissue quality and can undermine the commercial viability of the imaging process.

The present invention addresses this problem by applying an electric field to a sample as it is immersed in a staining solution. The electrical driving force facilitates and speeds the penetration of the stain into the tissue to significantly reduce tissue staining time. The time needed to stain a tissue may be reduced from a period of weeks, to hours.

Figure 1:
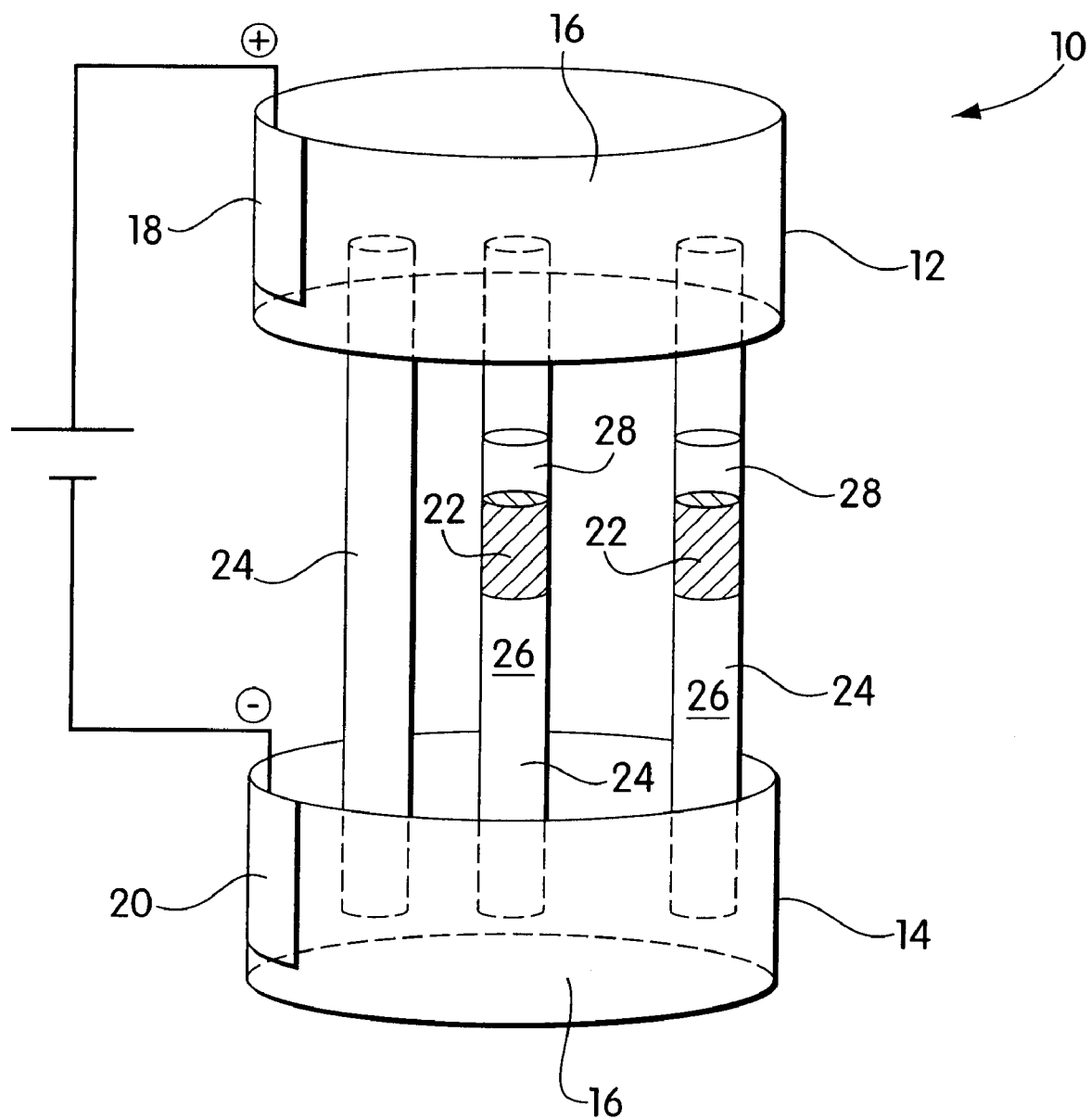
FIG. 1 is a schematic illustration of an electrophoresis unit useful in the practice of the invention.

The method may be practiced using a conventional tube cell electrophoresis assembly 10, as is shown in FIG. 1; however, it is contemplated that the method may employ any conventional assembly that restricts the flow of electricity to a narrow opening in which the tissue resides. The method uses electrodes and buffers commonly employed in electrophoresis.

The method is described with reference to an antibody which acts as a stain precursor and provides tissue specificity for the staining process. In preferred embodiments, the stain precursor is a primary antibody and a labeled secondary antibody having affinity for the primary antibody is introduced in a subsequent step.

The method may be used with any stain precursor or stain molecule having directed mobility in an electrical field. The molecule requires a charge in order to migrate in an applied electrical field. Molecules having no, or insufficient, charge may be modified by altering the pH, by chemical derivatization and the like, so as to provide the desired charge. All things being equal, the greater the net charge of the molecule, the greater its migration rate in an electric field.

With reference to FIG. 1, upper 12 and lower 14 reservoirs hold a buffer solution 16 and contain electrodes 18 and 20, respectively. Polarity of the electrodes may be normal or reversed in use, dependent on the overall charge of the antibody used as the staining molecule or stain precursor. The electrophoresis assembly includes one or more tubes 24 that are in electrical contact with the upper and lower reservoirs 12, 14. The electrophoresis apparatus may be capable of processing more than one sample at a time, as is shown in FIG. 1.

In one embodiment of the invention, a tissue sample 22 to be stained is prepared and introduced into tube 24. The tissue sample preferably is of similar dimension to and conforms to the shape of the inner diameter of the tube so that it sits securely within the tube. Tube dimensions are selected to accommodate the tissue sample to be stained. Tissue size can vary greatly, for example, from on the order of 100 microns, to millimeters, and up to a centimeter or even more. The tube is filled with an ionically conductive solution 26, which is typically a buffer. The particular solution is selected based on its physiological compatibility with the tissue sample and its pH (which will have an effect on the net charge, and therefore the mobility, of any antibody used in the electrophoretic staining process).

An antibody 28 is introduced into the tube. The antibody may be introduced with the tonically conductive solution or it may be added in a separate step. The antibody is preferably introduced in a separate step directly adjacent to the tissue as this procedure minimizes the amount of antibody needed to fully penetrate the tissue. For example, a concentrated antibody solution may be introduced first into the tube at a location adjacent to the tissue 22. Thereafter, buffer 26 may be added to fill the tube.

Alternatively, the antibody may be introduced into the tube in a solid medium, such as agarose. The antibody is first mixed with agarose to form a semisolid gel; and a plug is cut from the gel which then may be positioned adjacent to the tissue. In this embodiment, the antibody first diffuses from the gel before penetrating the tissue. Delivery of the antibody in this manner is advantageous, in that, the antibody is introduced into the tissue in a gradual manner.

In typical applications, the voltage is constant and the amperage is adjusted to obtain the desired antibody mobility. Under an applied electric field the antibody migrates in the direction of the tissue, enters the tissue and is immobilized upon complexation with a component of the tissue for which it has affinity. In this way, the tissue behaves as an affinity column for the stain. Electric field is maintained to complete penetration of the stain into the tissue interior. Voltage is on an order of 50–700V, and is preferably in the range of 100–400V.

Electrophoresis conducted within the parameters described herein above results in a substantially fully stained tissue sample, e.g., greater than 80% and preferably greater than 90%, in a matter of hours. Extent of tissue staining may be determined by removing one sample and determining the extent of antibody penetration. Testing may be carried out using conventional techniques. For example, the sample may be frozen in a cryostat using OCT. Thin sections (ca. 4 microns) may be cut and stained with secondary antibody and colorant substrate to determine the extent of primary antibody penetration. The electrophoresis process may be modified to improve the staining process based upon test results. Optimal staining conditions are determined empirically by observing the extent and nature of penetration and adjusting the electrophoresis parameters accordingly. Current may be increased to increase the extent of penetration or to decrease processing time. Tissue preparation techniques, such as fixation, etc. also may be altered to adjust the rate of antibody penetration.

According to the method described above, electrophoresis-induced staining of the tissue sample may be carried out in a simple buffer solution. The tissue sample provides sufficient mechanical support to retain the sample within the electrophoresis tube. In alternative embodiments, a gel support may be used to anchor the tissue in the tube. Exemplary media include agarose and polyacrylamide, and the like. It may be desirable to employ such media in circumstances where the tissue sample is smaller than the inner diameter of the tube such that the sample is not self-supporting. The semisolid gel used in electrophoresis can immobilize and support the undersized sample in the tube.

In another embodiment of the invention, the tissue sample is infiltrated with electrophoresis medium prior to its introduction into the tube. Infiltration is used herein to refer to treating the tissue with a liquid or series of liquids that penetrate throughout the tissue to the molecular level and are then transformed into a solid or a semisolid in order to render the sample rigid. In the current embodiment, infiltration with electrophoresis medium ensures that the stain passes uniformly through the tissue and does not migrate primarily through natural or artificial gaps or passages in the system which provide low resistance pathways.

Once the tissue sample is stained with a primary antibody, a secondary antibody also may be introduced by electrophoresis-induced staining. The sample is treated as described above, except that a secondary antibody is used in place of the primary antibody in the electrophoresis process., Alternatively, the secondary antibody may be introduced using conventional en bloc immersion techniques.

In another embodiment of the invention, primary and secondary antibodies, or a stain molecule and a stain precursor, may be applied to the tissue in a single step. To this end, a primary antibody and a secondary antibody are selected having opposing migratory behavior in an electric field, that is, when an electric field is applied, the two molecules will migrate simultaneously to opposite electrodes. The antibodies may be modified as discussed herein above to obtain the stated migratory behavior.

Figure 2:
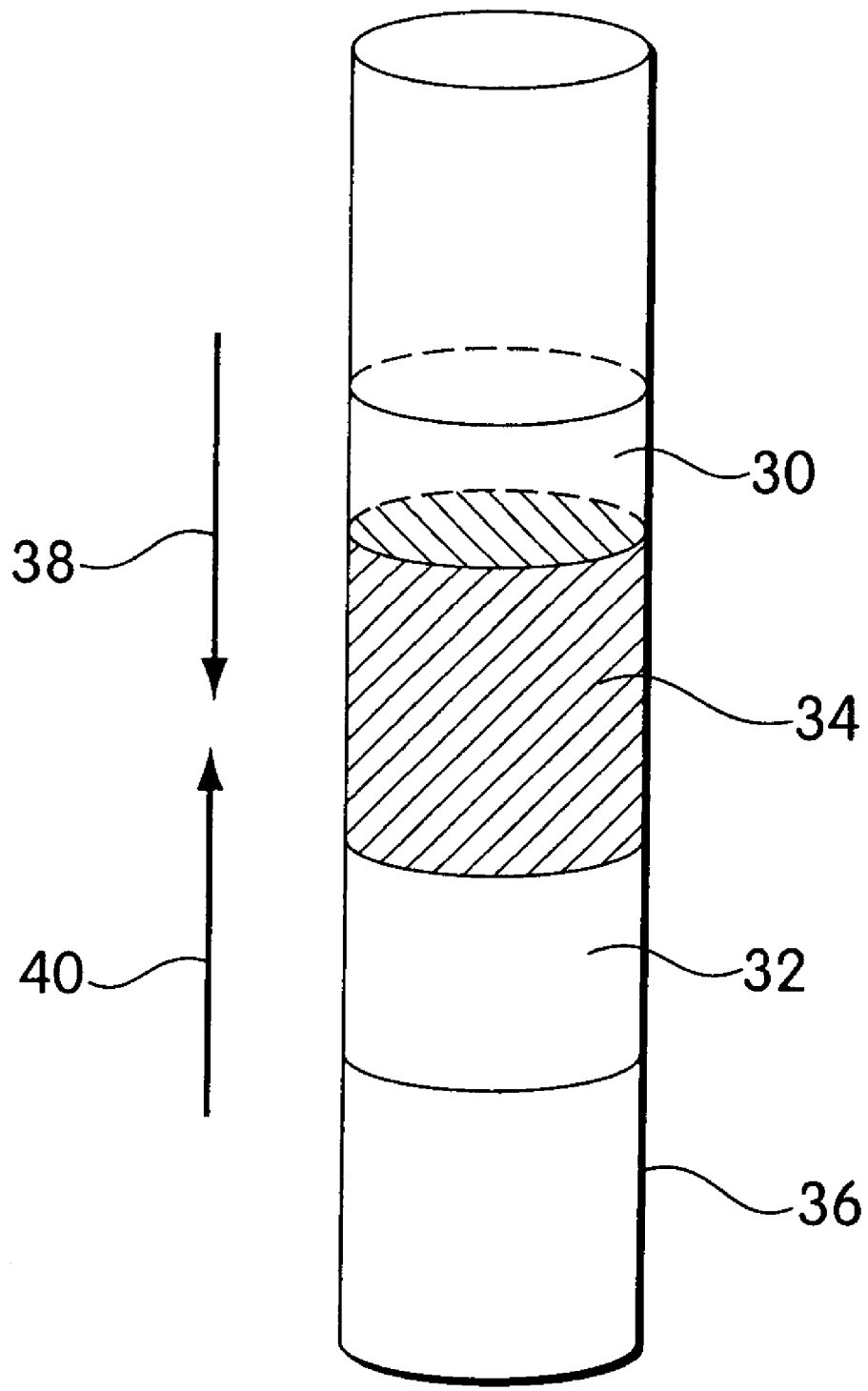
FIG. 2 is a schematic illustration of another embodiment of the invention in which a primary antibody and a secondary antibody are applied to the tissue in a single step.

Referring to FIG. 2, primary antibody 30 and secondary antibody 32 are positioned at opposite sides of a tissue sample 34 in an electrophoresis tube 36. The opposing ends of the tube are in electrical communication with electrodes (not shown) and a power source (not shown). When a voltage is applied, the primary and secondary antibodies 30, 32 migrate in opposite directions as indicated by arrows 38, 40, respectively. The relative positions of the primary and secondary antibodies and the tissue are selected such that the antibodies penetrate the sample and form a stain or stain precursor conjugate. In preferred embodiments, the primary antibody penetrates and binds to the tissue prior to the secondary antibody.

The present invention advantageously improves the quality of the stained image by reducing the level of background stain. The quality of the tissue image is influenced by the local antigen level and the level of background signal. Even high concentrations of antigen may be difficult to detect or distinguish against high background stain. Electrophoresis of the tissue sample induces mobility of all charged species and so prevents unbound antibody from persisting in the tissue. Thus, the tissue acts as an affinity column to bind the antibody stain while any unbound antibody is driven out of the tissue under the force of the electric field.

In most instances, there will be no clear advantage to using the method of the invention with conventional thin tissue sections, since in that case staining time is not unduly long. However, it may be desirable to combine electrophoresis- induce tissue staining with conventional tissue slide microscopy in those instances where high background staining would otherwise interfere with the imaging process. Thus, the whole tissue may be treated with primary antibody using the method of the invention to obtain an antibody-bound tissue. The tissue is then sectioned and treated with secondary antibody and a colorant in the conventional manner. Background staining is significantly reduced because excess unbound antibody is removed from the tissue during electrophoresis process.

According to the method described herein, either direct or indirect methods of detection may be employed. In direct detection, the primary antibody is labeled with a dye or colorant reagent and used directly as the imaging stain. In indirect detection methods, the primary antibody is unlabeled and its binding is detected by complexation with a secondary compound, such as a labeled secondary antibody. The same reagents may be used to label the secondary antibody as are available for use with the primary antibody. In addition, there is less risk of activity loss because the primary antibody is not being chemically modified. Alternatively, the secondary antibody may be complexed to an enzyme or other agent for conversion of a non-colored substrate to a colored substrate.

Most common labeling methods may be employed in the method of this invention. The stain may be a colored or fluorescent substance. Fluorescent or dark-field staining is accomplished using fluorescent dyes and standard or bright-field staining is accomplished using non-fluorescent dyes. Typical methods used in tissue staining to label the detecting agent include the use of fluorochromes and enzymes which react to form permanent colored or fluorescent products.

Higher sensitivity, but lower resolution, is found when using enzyme labels as compared to fluorescent labels. Enzyme-labeled reagents are detected using soluble chromogenic substrates that precipitate following enzyme reaction yielding an insoluble colored product at the enzyme location. Exemplary enzymes include horseradish peroxidase, alkaline phosphatase, and β-galactosidase.

In contrast, resolution of sub-cellular features is excellent when using fluorochrome-labeled antibodies. The drawback to this method is the relatively weak emission from the fluorochrome and the susceptibility of the fluorochrome to photo-bleaching. Exemplary fluorochromes include fluorescein, rhodamine and Texas red.

Another detection method involves the use of a biotin/streptavidin system. The primary antibody (or the secondary antibody) may be conjugated with biotin. Biotinylation can be carried out under mild conditions and does not normally adversely affect antigen binding. In order to detect the conjugate, labeled avidin or strepavidin is conjugated to the biotin. This method has the advantage of a facile labeling molecule, without the risk of loss of activity.

For further information on these and other tissue sample labeling methods, the interested reader is directed to "Antibodies: A Laboratory Manual" (E. Harlow and D. Lane, Cold Spring Harbor Laboratory, 1988), the content of which is incorporated in its entirety by reference.

Once the sample has been stained en bloc, it may be further treated in preparation for sectioning and examination. The tissue may be fixed with a chemical solution that preserves, hardens, and permeabilizes the sample and thereafter may be infiltrated with a liquid or series of liquids that penetrate throughout the tissue to the molecular level to transform the tissue into a solid or a semisolid in order to render the sample rigid. In order to obtain a viewable surface, the infiltrated tissue may be embedded by placing the infiltrated tissue in a mold and surrounding it with a substance (usually the same as the infiltrating substance) which is then hardened to form an encasing block. The embedding substance thus serves to provide rigid support and to facilitate the cutting process. Specimens for viewing may be obtained by cutting from the block thin slices that may then be mounted on glass slides or other support. Alternatively, the exposed face of the tissue block may be imaged using the method set forth in U.S. Pat. No. 4,960,330.

The method is described in the following examples, which are presented for the purposes of illustration and are not limiting of the invention.

EXAMPLE 1

Cylindrical plugs of tissue, approximately 4 mm in diameter and 2 mm in length, were prepared from human kidneys by use of a 4 mm biopunch from Fray. The kidney tissue was previously fixed in EXCELL preservative (MasterTech, Lodi, Calif.). The plugs were washed once for 10 minutes in distilled water on a rotator, and then were washed three times (10 minutes each) in 0.1 M HEPES Buffer (pH 7.5) with 0.5% Triton X-100 surfactant.

The Bio-Rad Model #175 tube cell electrophoresis assembly with a Bio-Rad power supply model Power Pac 300 was used for electrophoresis. Glass tubes of 125 mm in length and slightly less than 4 mm in width were used. The tubes were rinsed initially before use with 0.1 M HEPES buffer with 0.5% Triton X-100.

The lower chamber of the electrophoresis cell was filled with 0.1 M HEPES buffer with no detergent up to slightly below the overflow mark.

0.1 M HEPES buffer with 0.5% Triton X-100 was used only for antibody dilution and rinsing of the glass tubes. 0.1 M HEPES buffer with no detergent was used as an electrophoresis buffer during the experimental run. Approximately 3–4 liters of fluid were required to fill the upper and lower chambers of the tube cell apparatus. Novocastro anti-CD34, diluted 1:5 with 0.1HEPES buffer with 0.5% Triton X-100, was used as the primary antibody; and Southern Biotech goat anti-mouse IgG1-AP (AP=alkaline phosphatase) conjugate, diluted 1:5 with 0.1 M HEPES buffer with 0.5% Triton X-100, was used as the secondary antibody.

After initial tissue preparation, the plugs were carefully inserted into the glass tubes and were pushed into place approximately half-way down the tube by means of applicator sticks. The bottom space between the tissue plug and the end of the tube was filled with HEPES buffer using a syringe and needle and then was stoppered. The tube was then placed into the upper electrophoresis chamber and down into the lower chamber and the stoppers were removed. After all the tubes were thus processed and placed in the upper chamber, 100 μl of the primary antibody solution was layered onto the top of each tissue plug. Then a layer of HEPES buffer was carefully added over the antibody layer until the tube was completely full. Any unused channels in the electrophoresis apparatus were closed with rubber stoppers. The upper chamber was then filled to the edge of the electrode platform with HEPES buffer.

For the primary antibody, the voltage was set at 100V. The current depended on the number of tubes, but a minimum of 4 milliamps is considered necessary for the power supply used. Placement of extra dummy tubes filled with 1% agarose ensured the correct amperage when total number of samples run were less than three (from a total of four or more tubes). Due to the total charge of the primary antibody, the polarity of the electrodes was reversed prior to operation. Electrophoresis was conducted for six hours.

At the end of the run, a sample was removed and evaluated for extent of antibody penetration. The plug was rinsed with TRIS-HCL buffer (0.5M, pH 7.5, 3X, 10 min). The sample was then frozen by cryostat with OCT, and thin samples of approximately 4 microns were cut for treatment with secondary antibody and colorant. Detection was carried out using Vector Red (Vector Laboratories, Burlingame, Calif.).

In the human tissue, this process resulted in high specific staining of all blood vessels, including peritubular and glomerular capillaries. Penetration was up to 90% complete.

The secondary antibody was then added to the tissue. Prior to adding the secondary antibody, the plugs were rinsed with HEPES buffer in order to remove any remaining primary antibody. Plugs were rinsed at least three times with large quantities of buffer using a long needle and syringe. The tissue plugs were pushed to the far end of the glass tube with an applicator stick. A rubber stopper was placed on the other end of the tube and the tube was inverted so that now the direction of the tissue was reversed relative to its position using primary antibody. The bottom of the tube was filled as before with buffer and was placed in the electrophoresis chamber and the stopper was removed. 100 μl of goat anti-mouse IgG1-AP conjugated solution was carefully layered on top of the plug. The tube was then carefully filled to the top with HEPES buffer.

For penetration of the secondary antibody, the voltage was set to 200V. The current depended on the number of tubes, but a minimum of 4 milliamps was considered necessary with the power supply used. The polarity was not reversed. Electrophoresis was conducted for twelve hours.

Samples were removed for evaluation of stain penetration, as described above. Detection was carried out using Vector Red. This procedure resulted in highly specific staining of blood vessels with very little background signal. The extent of penetration of the secondary antibody was on the order of 15% which provided a sufficient degree of staining to give a high quality image. The method provided a high quality image with low background signal.

Altenatively, secondary antibody penetration was accomplished using conventional en bloc immersion techniques. The tissue was immersed in a secondary antibody staining solution for about one week. The tissue showed 100% stain penetration.

EXAMPLE 2

Human kidney tissue was prepared for examination as described above in Example 1 for staining according to the invention. An attempt was made to prepare samples from cortex tissue of the kidney, since different tissue types stain differently; however, tissue type varied somewhat. The tissue type of the samples is noted in Table 1.

Tissue electrophoresis was conducted using primary antibody Novocastro anti-CD34 as described in Example 1, except that voltage and time were varied. Voltage was set at 100, 200 and 300V and electrophoresis was conducted for 3, 6, 12, and 24 hours.

After electrophoresis, the tissue samples were removed and evaluated for extent of antibody penetration. The samples were rinsed with TRIS-HCL buffer (0.5M, pH 7.5, 3X, 10 min) and frozen by cryostat with OCT. Thin samples of approximately 4 microns were cut for treatment with secondary antibody and colorant. Detection was carried out using Vector Red.

Each sample was evaluated for extent of staining and the results are shown in Table 1. Samples bearing the same number represent tissue sections cut from the same tissue block.

The tissue sections were evaluated for total percent stained, percent understained; percent overstained and percent well stained. "Total percent stain" was determined by viewing the sample along the direction of staining, i.e. the long axis of the electrophoresis tube. Any staining along that axis was noted and included in total stain. Understaining represents the situation in which faint staining of the tissue is observed, but it is insufficient for proper imaging. The sample was considered overstained in those circumstances where non-specific or interstitial staining was observed. Well stained samples were those in which specific staining relating to antigen binding in the tissue was observed at a level sufficient for imaging.

The result are reported in Table 1.

| Sample No. | Tissue type | time (h) | voltage | % total stain | % under stained | % over stained | % well stained |
|---|---|---|---|---|---|---|---|
| 3a | C | 3 | 100 | 100 | 5 | 10 | 85 |
| 3b | C | 3 | 100 | 95 | 15 | 10 | 70 |
| 12a | C | 3 | 100 | 100 | 0 | 10 | 90 |
| 12b | C | 3 | 100 | 90 | 10 | 5 | 75 |
| 22a | C | 3 | 100 | 100 | 10 | 10 | 80 |
| 22b | C | 3 | 100 | 100 | 20 | 0 | 80 |
| 26a | C | 3 | 100 | 100 | 10 | 5 | 85 |
| 26b | C | 3 | 100 | 100 | 10 | 0 | 90 |
| 52a | J | 3 | 100 | 100 | 10 | 0 | 90 |
| 52b | C | 3 | 100 | 80 | 0 | 5 | 75 |
| 55a | J | 3 | 100 | 100 | 10 | 5 | 85 |
| 55b | C | 3 | 100 | 100 | 5 | 5 | 85 |
| 1a | J | 3 | 200 | 30 | 5 | 10 | 15 |
| 1b | J | 3 | 200 | 30 | 5 | 10 | 15 |
| 11a | C | 3 | 200 | 80 | 50 | 10 | 20 |
| 11b | C | 3 | 200 | 50 | 15 | 5 | 30 |
| 13a | C | 3 | 200 | 45 | 10 | 5 | 30 |
| 13b | C | 3 | 200 | 35 | 15 | 5 | 15 |
| 2a | C | 3 | 300 | 30 | 5 | 5 | 20 |
| 2b | M | 3 | 300 | 50 | 15 | 10 | 25 |
| 21a | M | 3 | 300 | 20 | 0 | 0 | 20 |
| 21b | J | 3 | 300 | 20 | 5 | 5 | 10 |
| 37a | C | 3 | 300 | 35 | 5 | 5 | 25 |
| 37b | M | 3 | 300 | 35 | 10 | 0 | 25 |
| 24a | C | 6 | 100 | 90 | 30 | 15 | 45 |
| 24b | C | 6 | 100 | 100 | 0 | 10 | 90 |
| 48a | C | 6 | 100 | 85 | 20 | 20 | 45 |
| 48b | C | 6 | 100 | 100 | 0 | 20 | 80 |
| 54a | C | 6 | 100 | 80 | 25 | 20 | 35 |
| 54b | C | 6 | 100 | 100 | 0 | 10 | 90 |
| 61a | C | 6 | 100 | 75 | 20 | 15 | 40 |
| 61b | J | 6 | 100 | 100 | 10 | 15 | 75 |
| 18a | J | 6 | 200 | 90 | 35 | 25 | 30 |
| 18b | C | 6 | 200 | 100 | 20 | 10 | 70 |
| 19a | J | 6 | 200 | 100 | 5 | 30 | 65 |
| 19b | C | 6 | 200 | 100 | 15 | 35 | 50 |
| 64a | C | 6 | 200 | 80 | 20 | 10 | 50 |
| 64b | J | 6 | 200 | 90 | 25 | 15 | 50 |
| 4a | M | 6 | 300 | 90 | 65 | 10 | 15 |
| 4b | C | 6 | 300 | 40 | 15 | 5 | 20 |
| 9a | M | 6 | 300 | 95 | 70 | 10 | 15 |
| 9b | C | 6 | 300 | 40 | 20 | 5 | 15 |
| 65a | M | 6 | 300 | 55 | 25 | 5 | 25 |
| 65b | C | 6 | 300 | 45 | 20 | 5 | 20 |
| 23a | J | 12 | 100 | 100 | 5 | 25 | 70 |
| 23b | C | 12 | 100 | 100 | 0 | 30 | 70 |
| 51a | C | 12 | 100 | 100 | 0 | 25 | 75 |
| 51b | C | 12 | 100 | 100 | 0 | 25 | 75 |
| 59a | C | 12 | 100 | 100 | 0 | 20 | 80 |
| 59b | C | 12 | 100 | 100 | 0 | 60 | 40 |
| 62a | C | 12 | 100 | 100 | 0 | 40 | 60 |
| 62b | C | 12 | 100 | 100 | 0 | 50 | 50 |
| 10a | J | 12 | 200 | 70 | 30 | 0 | 40 |
| 29a | C | 12 | 200 | 60 | 0 | 0 | 60 |
| 56a | C | 12 | 200 | 100 | 0 | 0 | 100 |
| 58a | J | 12 | 200 | 70 | 30 | 0 | 40 |
| 32a | J | 12 | 300 | 65 | 15 | 10 | 40 |
| 32b | M | 12 | 300 | 50 | 20 | 15 | 15 |
| 36a | M | 12 | 300 | 70 | 30 | 25 | 15 |
| 36b | M | 12 | 300 | 30 | 5 | 20 | 5 |
| 42a | M | 12 | 300 | 65 | 25 | 25 | 15 |
| 42b | M | 12 | 300 | 45 | 10 | 15 | 20 |
| 5a | C | 24 | 100 | 100 | 20 | 30 | 50 |
| 5b | C | 24 | 100 | 100 | 0 | 35 | 65 |
| 27a | C | 24 | 100 | 100 | 20 | 40 | 40 |
| 27b | C | 24 | 100 | 100 | 10 | 30 | 60 |
| 40a | C | 24 | 100 | 100 | 10 | 20 | 70 |
| 40b | C | 24 | 100 | 100 | 0 | 25 | 75 |
| 43a | C | 24 | 100 | 100 | 5 | 10 | 85 |
| 43b | C | 24 | 100 | 100 | 10 | 50 | 40 |
| 7a | C | 24 | 200 | 95 | 10 | 50 | 35 |
| 7b | J | 24 | 200 | 80 | 10 | 25 | 45 |
| 33a | C | 24 | 200 | 95 | 15 | 55 | 25 |
| 33b | C | 24 | 200 | 80 | 15 | 30 | 35 |
| 34a | C | 24 | 200 | 85 | 15 | 50 | 20 |
| 34b | C | 24 | 200 | 85 | 15 | 25 | 45 |
| 14a | C | 24 | 300 | 50 | 15 | 25 | 10 |
| 14b | C | 24 | 300 | 70 | 30 | 20 | 20 |
| 15a | C | 24 | 300 | 50 | 15 | 15 | 20 |
| 15b | C | 24 | 300 | 50 | 10 | 10 | 30 |

All samples showed some non-electrophoresis staining along the outer edges of the tissue sample; however such staining was minimal. The results indicate that stain penetration tended to improve with increased time, up to 1 hours. Interestingly, best stain penetration was observed at the lower voltage of 100V. This may be due to capacitance secondary effects at the higher voltages. The averaged results for each time and voltage condition are shown in Table 2.

TABLE 2

Percent stain penetration for particular time and voltage.

| | t | | | |
|---|---|---|---|---|
| V | 3.0 | 6.0 | 12.0 | 24.0 |
| 300 | 20.8% | 18.3% | 18.3% | 20.0% |
| 200 | 20.8% | 52.5% | 60.0% | 34.2% |
| 100 | 82.5% | 62.5% | 65.0% | 60.6% |

The above description of the invention is provided merely for the purpose of illustration of certain aspects and embodiments of the invention. Other embodiments will be apparent to the art skilled and are considered to be within the scope of the invention, which is set forth in the claims which follow.

What is claimed is:

1. A method for en bloc staining a sample, said method comprising the steps of:
   a) immersing the sample in a staining solution including (i) an ionically conductive solution, and (ii) a charged stain molecule and/or stain precursor that associates with a component of the sample;
   b) applying an electric field across the staining solution, whereby the stain molecule penetrates into the sample to produce an en bloc stained sample; and
   c) embedding said en bloc stained sample.

2. The method of claim 1, wherein the stain precursor is selected from the group consisting of antibodies, nucleic acid probes and lectins.

3. The method of claim 2, wherein the stain precursor is a primary antibody.

4. The method of claim 3, further comprising the steps of:
   c) immersing the primary antibody-containing sample in a staining solution including an tonically conductive solution and a charged secondary antibody that binds to the primary antibody; and
   d) applying an electric field across the staining solution, whereby the secondary antibody penetrates into the sample.

5. The method of claim 3, further comprising the step of:
   immersing the primary antibody-containing sample in a solution comprising a secondary antibody that binds to the primary antibody.

6. The method of claim 4 or 5, wherein the secondary antibody is labeled, said label comprising a component for producing coloration in the sample.

7. The method of claim 6, wherein the label comprises a fluorescent probe.

8. The method of claim 6, wherein the stain molecule comprises an enzyme reactive to form a permanent colored product.

9. The method of claim 1, wherein the stain molecule comprises a labeled carrier molecule, said carrier molecule selected from the group consisting of antibodies, nucleic acid probes and lectins and said label comprising a component for producing coloration in the sample.

10. The method of claim 9, wherein the label comprises a fluorescent probe.

11. The method of claim 9, wherein the stain molecule comprises an enzyme reactive to form a permanent colored product.

12. The method of claim 1, further comprising the steps of:
   infiltrating the sample with a gel support prior to immersing the sample in the staining solution.

13. The method of claim 12, wherein the gel support is selected from the group consisting of agarose and polyacrylamide.

14. The method of claim 1, wherein the staining solution is contained in a chamber and the sample substantially occupies and conforms to the cross-sectional area of the chamber.

15. The method of claim 1, wherein a voltage in the range of 100–400V is applied.

16. The method of claim 15, wherein a voltage in the range of 50–700V is applied.

17. The method of claim 1, wherein the electric field is maintained for a time in the range of 1 to 25 hours.

18. The method of claim 1, wherein the electric field is maintained in the range of 3 to 15 hours.

19. The method of claim 1, further comprising the step of (d) sectioning said embedded en bloc stained sample.

20. A method for reducing unbound stain molecule in a sectioned tissue, said method comprising the steps of:
   a) immersing the a tissue sample in a staining solution including an ionically conductive solution and a stain precursor that associates with a component of the sample; and
   b) applying an electric field across the staining solution, whereby penetration of the stain precursor into the sample and emigration of unbound stain precursor from the sample occurs.

* * * * *